United States Patent
Sunkara et al.

(10) Patent No.: US 11,254,880 B2
(45) Date of Patent: Feb. 22, 2022

(54) DESULFURIZATION AND SULFUR TOLERANT HYDROGENATION PROCESSES OF HYDROCARBON FEEDSTOCKS

(71) Applicant: Advanced Energy Materials, LLC, Louisville, KY (US)

(72) Inventors: Mahendra Sunkara, Louisville, KY (US); Sivakumar Vasireddy, Louisville, KY (US); Juan He, Louisville, KY (US)

(73) Assignee: Advanced Energy Materials, LLC, Louisville, KY (US)

(*) Notice: Subject to any disclaimer, the term of this patent is extended or adjusted under 35 U.S.C. 154(b) by 0 days.

(21) Appl. No.: 16/841,405

(22) Filed: Apr. 6, 2020

(65) Prior Publication Data
US 2020/0231882 A1 Jul. 23, 2020

Related U.S. Application Data

(63) Continuation-in-part of application No. 16/481,714, filed as application No. PCT/US2018/017355 on Feb. 8, 2018.

(Continued)

(51) Int. Cl.
*B01J 23/10* (2006.01)
*C10G 25/00* (2006.01)
(Continued)

(52) U.S. Cl.
CPC ....... *C10G 25/003* (2013.01); *B01D 19/0005* (2013.01); *B01J 20/0225* (2013.01); *B01J 20/0244* (2013.01); *B01J 20/06* (2013.01); *B01J 20/08* (2013.01); *B01J 20/28023* (2013.01); *C07C 5/11* (2013.01); *C10G 2300/1003* (2013.01); *C10G 2300/104* (2013.01); *C10G 2300/1044* (2013.01);
(Continued)

(58) Field of Classification Search
CPC ... B01J 20/06; B01J 20/08; B01J 20/12; B01J 20/28007; B01J 20/28023; B01J 20/3078; B01J 20/3085; B01J 23/755; B01J 23/883; B01J 35/0013; B01J 37/08; C10G 25/003; C10G 29/04; C10G 29/16; C10G 2300/202
USPC ....................................................... 502/307
See application file for complete search history.

(56) References Cited

U.S. PATENT DOCUMENTS

2010/0025301 A1   2/2010   Borgna et al.

FOREIGN PATENT DOCUMENTS

CN   104277874 A   1/2015
WO   2008137463 A2   11/2008

OTHER PUBLICATIONS

Gupta, M. et al. Nanowire catalysts for ultra-deep hydrodesulfurization and aromatic hydrogenation. Applied Catalysis B: Environmental, 2016, 180:246-254.

*Primary Examiner* — Haytham Soliman
(74) *Attorney, Agent, or Firm* — Law Office of J. L. Simunic

(57) ABSTRACT

The present invention relates to the use of adsorbents comprising zinc oxide nanowires decorated with catalytically active metal particles for the removal of sulfur from hydrocarbon feedstocks, including the desulfurization of diesel fuels and the deep desulfurization of natural gas, and to the use of decorated zinc oxide nanowire adsorbents for the hydrogenation of naphthalene selectively to tetralin in (Continued)

the presence of sulfur compounds. The adsorbent comprises nickel metal particles or nickel-zinc alloy particles deposited on zinc oxide nanowires.

13 Claims, 4 Drawing Sheets

Related U.S. Application Data

(60) Provisional application No. 62/457,695, filed on Feb. 10, 2017.

(51) Int. Cl.
  *B01J 20/06* (2006.01)
  *B01J 20/02* (2006.01)
  *B01J 20/28* (2006.01)
  *B01J 20/08* (2006.01)
  *C07C 5/11* (2006.01)
  *B01D 19/00* (2006.01)

(52) U.S. Cl.
  CPC ............. *C10G 2300/1051* (2013.01); *C10G 2300/1055* (2013.01); *C10G 2300/1059* (2013.01); *C10G 2300/202* (2013.01); *C10G 2300/207* (2013.01); *C10G 2300/4018* (2013.01)

DESULFURIZATION AND SULFUR TOLERANT HYDROGENATION PROCESSES OF HYDROCARBON FEEDSTOCKS

CROSS-REFERENCE TO PRIOR APPLICATIONS

The present application claims priority to U.S. Patent Application 62/457,695 filed 2017-February-10, and to PCT/US18/17355 filed 8 Feb. 2018, and to U.S. patent application Ser. No. 16/481,714 filed 29 Jul. 2019, currently, all of which are incorporated by reference in their entireties.

GOVERNMENT INTEREST

This invention was made with government support under grant number SC0015808 awarded by the U.S. Department of Energy. The government has certain rights in the invention.

FIELD OF THE INVENTION

The present invention relates to the use of adsorbents comprising metal oxide nanowires decorated with catalytically active metal particles for (1) the removal of sulfur from diesel fuel and other hydrocarbon feedstocks; (2) the selective hydrogenation of naphthalene to tetralin in the presence of sulfur compounds; and, (3) the deep desulfurization of natural gas in a one-step process.

BACKGROUND OF THE INVENTION

Sulfur compounds in liquid hydrocarbon fuels can oxidize to $SO_x$ species and cause air pollution. Various regulations now mandate lowering the sulfur levels in motor fuels, such as gasoline and diesel, to less than 10 ppm. In addition, the presence of sulfur compounds in fuel oils can cause catalyst deactivation and corrosion in refining processes. This can create a commercial challenge because it is projected that the global demand for ultra-low sulfur diesel (ULSD; Sulfur=10-15 ppm) will increase remarkably as more countries worldwide implement severe sulfur specifications. To achieve this, refiners will be required to upgrade poor quality feedstocks, such as light cycle oil (LCO), heavy gas oils, and sour crude products, to produce the required volumes of ULSD.

On-board reformers to power fuel cells in motor vehicles are becoming more popular as the public seeks more efficient energy sources. The on-board reformer enables the rapid and efficient delivery of hydrogen from a fuel source, such as natural gas, liquefied petroleum gas, landfill gas, digester gas, gasoline, diesel and jet fuel. However, these fuels contain sulfur as an impurity. The sulfur must be nearly completely (sulfur <50 ppb) removed to prevent poisoning of the reforming catalyst and fuel cell anode catalyst.

Natural gas contains 1-2 ppm $H_2S$ in addition to other sulfur species, such as carbonyl sulfide (COS), mercaptans (methyl mercaptan, ethyl mercaptan and butyl mercaptan) and thiophene, which account for another 3-4 ppm. For nearly any commercial application, the sulfur level in natural gas must be reduced to less than 100 ppb.

However, the removal of sulfur compounds from the hydrocarbon feedstock can provide a challenge in petroleum refining. For example, refractory thiophenic sulfur compounds are particularly difficult to remove. The prior art method requires a catalytic hydrodesulfurization process (HDS) in a trickle bed reactor operated at elevated temperatures (300-400° C.) and pressures (20-100 atm, $H_2$) using Co—Mo/$Al_2O_3$ and Ni—Mo/$Al_2O_3$ catalysts. The HDS process is effective in removing thiols, sulfides, and disulfides, but less efficient for thiophenes and thiophene derivatives. Moreover, the HDS process emits $H_2S$ gas which requires further downstream processing to eventually convert the $H_2S$ gas to elemental sulfur.

Noble metal catalysts can be employed with high performance at low temperature in the hydrogenation of aromatics, but are easily poisoned by sulfur compounds even at the ppm level. In the hydrogenation processes, it is common to use a two-stage hydrotreating process wherein the sulfur content of a feedstock is first reduced to a level of less than 2 ppm by ultra-deep hydrodesulfurization and then hydrogenation of aromatics in the feedstock is conducted in the second stage by using a noble metal catalyst. Unfortunately, the reduction of sulfur content in diesel fuel or crude oil derived chemicals to less than 2 ppm with HDS process is quite difficult and requires a huge investment.

Polishing processes, such as reactive adsorption, selective adsorption, oxidation/extraction desulfurization, or ultrasonic desulfurization, may be used to supplement the conventional HDS process. The oxidation/extraction desulfurization polishing processes have undesirable side reactions that reduce the quality and quantity of the fuel. The adsorption processes are attractive because of the straightforward operating conditions and availability of inexpensive and re-generable adsorbents. However, only a few adsorbents have shown high selectivity for difficult to hydrotreat sulfur compounds.

Thus, it would be beneficial to have a catalyst that is effective for removal of sulfur from liquid fuels, gas-phase naphtha, natural gas and feed gas for fuel cell applications. It would be particularly beneficial to have a catalyst effective for use in sulfur tolerant hydrogenation processes.

SUMMARY OF THE PRESENT INVENTION

The present invention is a method for removing sulfur from hydrocarbon feedstocks and for performing hydrogenation reactions in sulfur-contaminated feedstocks, including the hydrogenation of naphthalene in the presence of sulfur compounds, using catalysts or adsorbents comprising metal oxide nanowires decorated with catalytically-active metal particles. In a preferred embodiment, the adsorbent comprises zinc oxide nanowires decorated with catalytically-active metals selected from nickel, cobalt, molybdenum, platinum, palladium, copper, oxides thereof, alloys thereof, and combinations thereof.

Sulfur is removed from gas and liquid feeds using the decorated metal oxide nanowire adsorbents or nanometal oxide adsorbents. In some embodiments, the sulfur is removed through a desulfurization process in a fixed bed reactor. In some embodiments, the sulfur is removed through a desulfurization process in a batch reactor. In some embodiments, the sulfur is removed through a desulfurization process with an external hydrogen supply. In some embodiments, the sulfur is removed through a desulfurization process without an external hydrogen supply. The process is effective for the removal of sulfur from diesel fuels and liquid fuel stream reducing the sulfur concentration from about 130-200 ppm by weight to approximately 15 ppm by weight without generating undesirable $H_2S$ gas. The one-step process is effective for the deep desulfurization of natural gas stream reducing the sulfur concentration from about 3-20 ppm by weight to less than 15 ppb by weight.

The nanometal oxide adsorbents are also effective for the selective hydrogenation of naphthalene to tetralin in the presence of sulfur compounds. For example, a naphthalene feedstock having a sulfur content of 300 ppm or lower can be subjected to a hydrogenation reaction using the nanometal oxide adsorbents to selectively produce tetralin or decalin, depending on process conditions.

DETAILED DESCRIPTION OF THE PRESENT DEVELOPMENT

Figure 1:
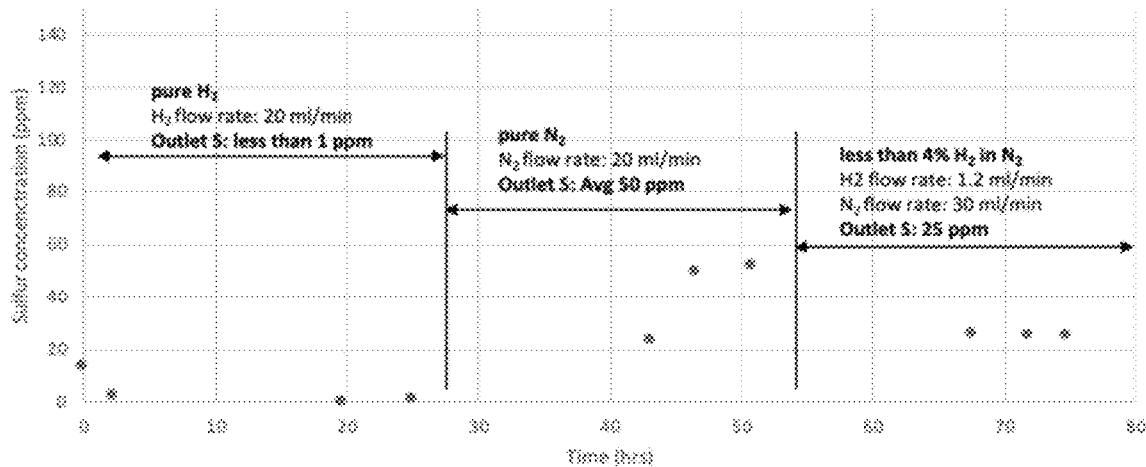
FIG. 1 is a graph showing the sulfur level reduction in refinery diesel fuel using a Ni/ZnO adsorbent at P=25 bar, T=290° C., LHSV=0.8 h$^{-1}$.

The present development is a catalyst composition and methods for using the catalyst composition. The catalyst composition is an adsorbent comprising a metal oxide nanowire decorated with catalytically-active metal particles. In some embodiments described herein, the catalyst composition is an adsorbent comprising a zinc oxide nanowire decorated with nickel particles or nickel-zinc alloy particles. As used herein, the term "catalyst(s)" may be used interchangeably with the term "adsorbent(s)" when referring to the inventive composition. As used herein, the phrase "decorated nanowire adsorbent(s)" may be used interchangeably with the term "nanometal adsorbent(s)" when referring to the inventive composition. As used herein, the term "decorated" means to bind to the specified metal or metal oxide or metal alloy to the surface of the nanowire.

The catalyst composition or adsorbent is prepared by loading catalytically-active metal particles onto metal oxide nanowires. The metal oxide nanowire preferably comprises zinc oxide. A preferred method for the production of zinc oxide nanowires is taught by Sunkara et al. in US Published Application 2012/0027955, which is incorporated herein in its entirety by reference. In a preferred embodiment, the metal oxide nanowire comprises from about 55 wt % to about 88 wt % of the adsorbent composition.

Exemplary catalytically-active metals include nickel, nickel-zinc alloys, cobalt, molybdenum, platinum, copper, nickel-copper alloys, and combinations thereof. Catalytically-active metals, are loaded onto the metal oxide nanowires via wet impregnation or incipient wetness techniques, as is known in the art. In a preferred embodiment, the adsorbents are prepared by conventional impregnation techniques using aqueous solution of metal nitrates or acetates. The catalytically-active metal may be in the form of an elemental metal or an oxide. Without being bound by theory, it is believed that the catalytically-active metals are present on the surface of the nanowires as particles. Representative examples of catalytically-active metals on a zinc oxide nanowire support include, but are not limited to Ni/ZnO, Ni$_{1-x}$Zn$_x$/ZnO, Ni—Cu/ZnO, Ni$_{1-x}$Cu$_x$/ZnO, Ni—Co/ZnO, Ni—Mo/ZnO, Ni—Pt/ZnO, Ni/ZnO—Al$_2$O$_3$.

Catalytically-active metal loading may vary from about 3 wt % to about 20 wt %. In a preferred embodiment, a first catalytically-active metal is loaded onto a metal oxide nanowire at a concentration of from about 3 wt % to about 20 wt %, and more preferably at a concentration of from about 6 wt % to about 15 wt %, and most preferably at a concentration of from about 12 wt %, and a second catalytically-active metal is loaded onto the metal oxide nanowire at a concentration of from about 0 wt % to about 12 wt %, and most preferably at a concentration of from about 6 wt %. In an exemplary embodiment, the first catalytically-active metal is nickel and the second catalytically active metal is selected from the group consisting of zinc, palladium, platinum, cobalt, molybdenum, copper, and combinations thereof.

Optionally, as is known in the art, a binder, such as alumina, bentonite clay or combinations thereof, may be added to the paste to improve crushing strength. In an exemplary embodiment, alumina is added to the composition at a concentration of from about 0 wt % to about 30 wt %.

The catalytically-active metal loaded metal oxide nanowire, or adsorbent, may be dried and formed into extrudates and calcined. Suitable drying temperatures will depend on the particular adsorbent, but a general range would be from about 100° C. to about 150° C., and preferably at about 120° C. Suitable calcining temperatures will depend on the particular adsorbent, but a general range would be from about 400° C. to about 500° C., and preferably at about 430° C. Exemplary extrudates are cylindrical shaped with diameters of about 1.2 mm to 4.5 mm. It is anticipated that the catalyst can be extruded into a trilobe shape and other shapes and extrudate sizes that are known in the art. In a preferred embodiment, the extrudates are about 1.2 mm in diameter and about 5 mm to 10 mm in length, and the extruded adsorbent is calcined in a furnace at a temperature of from about 400° C. for a period of about 2 hours.

The nickel-decorated zinc oxide nanowire adsorbent is useful for the desulfurization of liquid fuel feedstocks and hydrocarbon feedstocks, such as waste lube oil, transmix fuels, diesel fuel, gasoline, naphtha, light cycle oil, diesel, jet fuel, kerosene, and combinations thereof. As used herein, the term "desulfurization" refers to the reduction of the sulfur level in a feedstock stream. As used herein, the term "deep desulfurization" means to reduce the sulfur level in a feedstock stream to a level equal to or less than 30 ppmv or less. As used herein, the term "ultra-deep desulfurization" means to reduce the sulfur level in a feedstock stream to a level equal to or less than 10 ppmv or less. The Ni/ZnO adsorbent of the present invention is effective for sulfur pickup at significantly higher levels than prior art catalysts or adsorbents. Specifically, the Ni/ZnO adsorbent of the present invention has a sulfur pickup equal to or greater than 150 mg S/g catalyst, and more preferably has a sulfur pickup equal to or greater than 180 mg S/g catalyst, and most preferably has a sulfur pickup equal to or greater than 220 mg S/g catalyst. Using the Ni/ZnO adsorbent to treat a gasoline feedstock reduces the sulfur level from 300 ppm down to <5 ppm, and results in fuel upgrading (increased cetane number) by increasing the cetane number from 48 to 60. Using the Ni/ZnO adsorbent to treat a naphtha feed having 1000 ppm thiophene sulfur at 350° C. and 20 bar results in deep desulfurization with the sulfur level after treatment at <5 ppm sulfur, and shows the adsorbent has a pickup capacity equal to 20 wt %.

The decorated ZnO adsorbent is also useful for the deep desulfurization of natural gas streams in a single step process. Natural gas contains 4-6 ppm sulfur in the form of $H_2S$, COS, methyl mercaptan, ethyl mercaptan and $^t$butyl mercaptan, and thiophene, as the major sulfur species. Deep desulfurization, reducing the sulfur level to less than 100 ppb, is necessary for most commercial applications. Traditionally, this is achieved by desulfurizing the natural gas to a sulfur level of about 2 ppm, and the using a second step to further reduce the sulfur level to the ppb range. However, because of the pickup capacity of the decorated ZnO adsorbent, the sulfur level of a natural gas stream initially having 6-7 ppm sulfur can be reduced to a level of <15 ppb in a single pass. Eliminating the need for a second desulfurization step enhances the utility of natural gas for processes such as fuel cell manufacturing processes, in ammonia production, and in fertilizer production.

The Ni/ZnO adsorbents are also effective for the selective hydrogenation of naphthalene to tetralin in the presence of sulfur compounds. As is known in the art, the naphthalene feed from a refinery can contain sulfur at levels as high as 4000 ppm and traditional hydrotreatment using conventional HDS catalysts can reduce the sulfur level down to ~100 ppm. Using the NiZn/ZnO nanowire adsorbent, a naphthalene stream having a sulfur level of 300 ppm or lower can be hydrogenated to tetralin or decalin selectively depending on process conditions, while entrapping sulfur into the ZnO support. This approach uses non-noble metal catalysts and has the capability to sustain the hydrogenation activity for the feed with sulfur as high as 300 ppm.

The following examples are intended to provide the reader with a better understanding of the invention. The examples are not intended to be limiting with respect to any element not otherwise limited within the claims.

Example 1

12% Ni-88% ZnO is prepared by dispersing 8.8 g of ZnO nanowires in distilled $H_2O$ and subjecting the nanowires to sonication for about 5 minutes. An aqueous solution of 7.62 g nickel acetate tetrahydrate is then added dropwise while stirring and while maintaining the nanowire solution pH at 9.0 using $NH_4OH$ solution. Stirring is continued for about 20 min after completion of addition and the nanowire nickel acetate solution is held in an oven at about 80° C. for approximately 15 hours. The oven temperature is then raised to about 150° C. and held at 150° C. for 3 h until a thick paste forms. The paste is then extruded and the extrudates are dried at about 150° C. for approximately 1 hour. The dried extrudates are then calcined at about 400° C. for approximately 2 h in static air.

Example 2

12% Ni-58.7% ZnO-29.3% $Al_2O_3$ is prepared according to the method of Example 1 except 8.8 g of ZnO nanowires and 4.39 g of γ-$Al_2O_3$ powder are dispersed in distilled $H_2O$ and the aqueous solution comprises 7.62 g nickel acetate.

Example 3

12% Ni-58.7% ZnO-29.3% $Al_2O_3$ is prepared according to the method of Example 1 except the nickel acetate solution is adjusted to pH 9 with $NH_4OH$ solution before addition to the nanowire solution.

Example 4

6% Ni-6% Co-58.7% ZnO-29.3% $Al_2O_3$ is prepared according to the method of Example 1 except 8.8 g of ZnO nanowires and 4.39 g of y-$Al_2O_3$ powder are dispersed in distilled $H_2O$ and the aqueous solution comprises 3.81 g nickel acetate and 3.8 g of cobalt acetate tetrahydrate.

The nickel decorated zinc oxide adsorbents were tested for sulfur removal under varying conditions. The desulfurization testing is done using either a model hydrocarbon stream spiked with from about 100 ppm to about 500 ppm sulfur by weight with an assortment of refractory sulfur species to closely resemble industrial conditions or with a diesel fuel sample obtained from an oil refinery and having about 100 ppm to about 500 ppm sulfur by weight and further containing an assortment of refractory sulfur species to closely represent industrial conditions. To perform the testing, fresh adsorbent—the metal coated nanowires—is packed into a stainless steel fixed bed reactor. To improve contact of the hydrocarbon feedstock that is to be subjected to desulfurization it is recommended that the adsorbents be extruded as particles with dimensions of about 1.2 mm-4 mm diameter, and preferably from about 2 mm-4 mm diameter, and a length of about 5 mm-10 mm.

The adsorbent is pretreated by heating the reactor to a temperature of about 150° C. and flowing nitrogen gas ($N_2$) over the adsorbent bed for about 2 hours and then reducing the adsorbent by starting a flow of hydrogen gas ($H_2$) over the adsorbent bed as the reactor temperature is raised over a period of about 2 hours from a temperature of about 150° C. at a temperature of between about 410° C. and about 430° C. and then holding the adsorbent bed at 430° C. with a $H_2$ gas flow, preferably 4% $H_2$ gas flow, for an additional 2 hours to 4 hours. Following pretreatment and reduction, the reactor temperature is cooled to a desulfurization temperature of 220° C. to about 425° C., more preferably at 290° C. to 300° C. Using 4% $H_2$ gas flow, the fixed-bed reactor is pressurized to 5-30 bar, more preferably at 15-20 bar. The hydrogen flow is stopped when the desired process temperature is reached.

A hydrocarbon feedstock then passes through the adsorbent at atmospheric pressure and at a liquid hourly space velocity (LHSV) of 0.5 $h^{-1}$ to 4 $h^{-1}$, more preferably at a LHSV of 1 $h^{-1}$ to 2 $h^{-1}$, most preferably at a LHSV of 1 $h^{-1}$. The hydrocarbon feedstock may be a sulfur containing liquid hydrocarbon, such as waste lube oil, transmix fuels, diesel fuel, gasoline, naphtha, kerosene. To best replicate actual industrial conditions, the waste lube oil tested had a starting thiophenic sulfur concentration of from about 500 ppm to about 1500 ppm an including about 50 ppm to 100 ppm of refractory sulfur compounds such as benzothiophene, dibenzothiophene, 4,6-dimethyldibenzothiophene; the transmix fuels had a starting sulfur concentration of from about 1000 ppm to about 1500 ppm; and the diesel fuel had a starting sulfur concentration of from about 500 ppm to about 1500 ppm. The solid impurities are filtered off prior to desulfurization. In a preferred embodiment, a 2-stage process is used wherein the feedstock passes through the adsorbent in a first stage to reduce the sulfur level to less than about 200 ppm and then the reduced sulfur feedstock passes through a bed of fresh adsorbent a second time to further reduce the sulfur concentration.

Example 5

15 g of the 12% Ni-58.7% ZnO-29.3% $Al_2O_3$ adsorbent from Example 3 is packed into a fixed bed reactor along with 5 g activated carbon and 5 g molecular sieves 13×, with the materials packed into the reactor such that the feedstock initially contacts the activated carbon and then the molecular sieves 13× and then the adsorbent, and then the feedstock exits the reactor. Prior to introduction of the feedstock, the adsorbent is pretreated and reduced, and the hydrogen gas flow is stopped. The reactor is then heated to a temperature of about 390° C. and atmospheric pressure. The hydrocarbon feedstock, a waste lube oil with 900 ppm sulfur, is preheated to vaporize the feedstock. The feedstock is pumped from a bottom inlet of the reactor and passes through the adsorbent at a liquid hourly space velocity of 1 to 3 $h^{-1}$ before exiting at a top outlet of the fixed bed reactor and condensing to a liquid. Table 2 shows the sulfur concentration from samples recovered at the outlet after various times on-stream.

TABLE 2

| Time on stream (h) | LHSV ($h^{-1}$) | Sulfur concentration at outlet (ppm) |
|---|---|---|
| 4.3 | 1 | 203.99 |
| 7.8 | 2 | 127.2 |
| 11.5 | 3 | 167.2 |

Example 6

The feedstock exiting the outlet from Example 5 is then fed through fresh 12% Ni-58.7% ZnO-29.3% $Al_2O_3$ adsorbent in a reactor and under the same conditions as described in Example 5 to further reduce the sulfur concentration. Table 3 shows the sulfur concentration from samples recovered at the outlet after various times on-stream from this second-stage processing.

TABLE 3

| Time on stream (h) | LHSV ($h^{-1}$) | Sulfur concentration at outlet (ppm) |
|---|---|---|
| 3.5 | 2 | 53.5 |
| 12.2 | 1 | 67 |
| 14.5 | 1 | 76 |
| 6.6 | 0.5 | 58.5 |
| 18.7 | 0.5 | 43.8 |
| 25.2 | 0.5 | 47 |

Example 7a

Example 5 is repeated with 17.5 g of the 12% Ni-58.7% ZnO-29.3% $Al_2O_3$ adsorbent, and the waste lube oil feedstock is replaced with a diesel feed obtained from a local gas station spiked to 470 ppm sulfur with 95% thiophene and 5% a combination of benzothiophene (BT), dibenzothiophene (DBT), 4,6-dimethyldibenzothiophene (DMDBT), and 4-methyldibenzothiophene (MDBT). More than 95% of thiophenes and benzothiophenes are removed during 48 hours of operation.

Example 7b

Example 70 is repeated with 17.5 g of the 6% Ni-6% Mo-58.7% ZnO-29.3% $Al_2O_3$ adsorbent, and the waste lube oil feedstock is replaced with a diesel feed obtained from a local gas station spiked to 470 ppm sulfur with 95% thiophene and 5% a combination of benzothiophene (BT), dibenzothiophene (DBT), 4,6-dimethyldibenzothiophene (DMDBT), and 4-methyldibenzothiophene (MDBT). More than 95% of thiophenes and benzothiophenes are removed during 24 hours of operation.

Example 8

Example 5 is repeated except 30 g of the 12% Ni-58.7% ZnO-29.3% $Al_2O_3$ adsorbent containing 15 wt % alumina binder is used. The waste lube oil with 900 ppm sulfur is vaporized and passes through the adsorbent at a LHSV of 0.5 $h^{-1}$ before exiting at a top outlet of the fixed bed reactor and condensing to a liquid. Table 4 shows the sulfur concentration from samples recovered at the outlet after various times on-stream.

TABLE 4

| Time on stream (h) | LHSV ($h^{-1}$) | Sulfur concentration at outlet (ppm) |
|---|---|---|
| 18 | 0.5 | 58.5 |
| 31.2 | 0.5 | 51.4 |
| 42.3 | 0.5 | 43.8 |

Example 9

Example 5 is repeated except the 5 g activated carbon and 5 g molecular sieves 13× are replaced with Selexsorb® with ⅛" diameter spheres from BASF, and the waste lube oil feedstock is replaced with terapure oil (T-120) oil with 900 ppm sulfur and the feedstock passes through the adsorbent at a LHSV of 1 $h^{-1}$. Table 5 shows the sulfur concentration from samples recovered at the outlet after various times on-stream.

TABLE 5

| Time on stream (h) | LHSV ($h^{-1}$) | Sulfur concentration at outlet (ppm) |
|---|---|---|
| 4 | 1 | 263.602 |
| 6.333 | 1 | 61.184 |
| 11.683 | 1 | 13.565 |
| 23.750 | 1 | 19.625 |
| 32.167 | 1 | 27.860 |

Example 10

30 g of the 12% Ni-88% ZnO adsorbent from Example 1 is packed into a fixed bed reactor along with 5 g activated carbon and 5 g molecular sieves 13×, with the materials packed into the reactor such that the feedstock initially contacts the activated carbon and then the molecular sieves 13× and then the adsorbent, and then the feedstock exits the reactor. Prior to introduction of the feedstock, the adsorbent is pretreated in $N_2$ at 150° C. for about 2 hours and then the adsorbent is reduced at 430° C. for an additional 2 hours, and the hydrogen gas flow is stopped. The reactor is then heated to a temperature of 300° C. and atmospheric pressure. The hydrocarbon feedstock, a diesel fuel from a refinery in Australia having a sulfur level of 200 ppm comprising various refinery sulfur compounds, including benzothiophene, dibenzothiophene, 4,6-dimethyldibenzothiophene, is pumped from a bottom inlet of the reactor and passes through the adsorbent at a LHSV of 1 to 2 $h^{-1}$ before exiting at a top outlet of the fixed bed reactor and being collected. As shown in FIG. 1, using the method of the present invention, the sulfur level is reduced in the diesel fuel from 200 ppm to less than 25 ppm.

Example 10A

Figure 2:
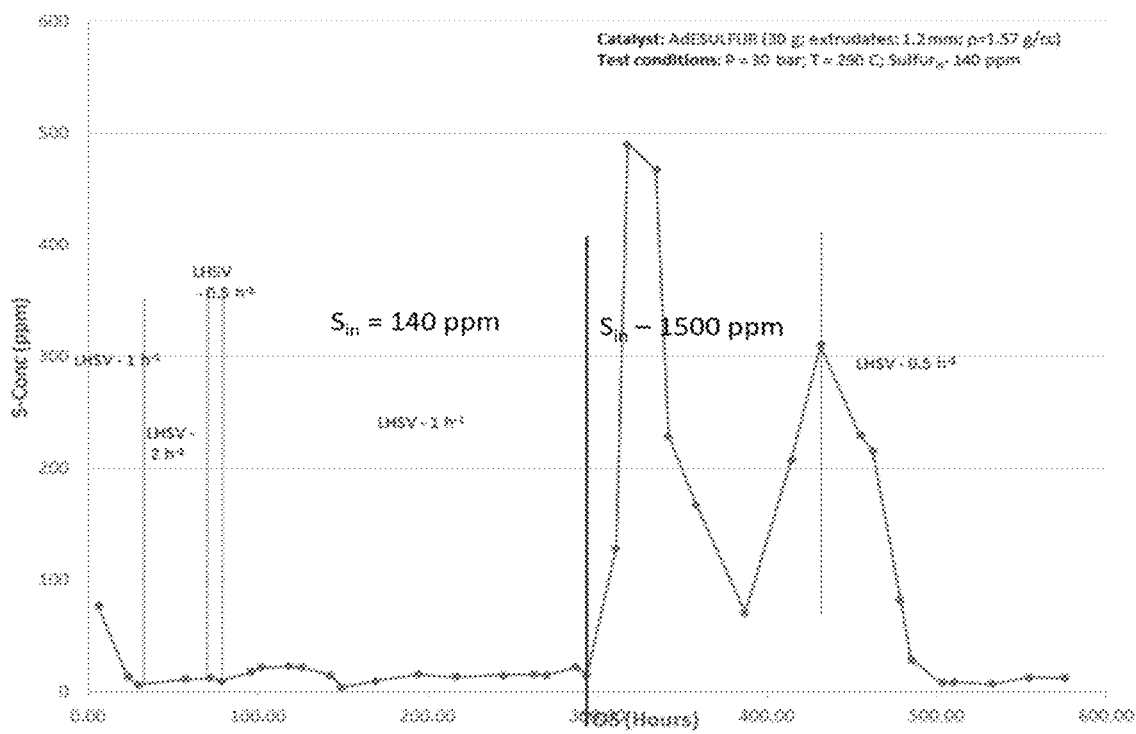
FIG. 2 is a graph showing the sulfur level over time for the ultra-deep desulfurization of diesel process using a Ni/ZnO adsorbent at P=30 bar, T=290° C., LHSV=variable.

To demonstrate that the process of the present invention can perform ultra-deep desulfurization and can be used as a polishing/upgrading technology in conjunction with hydrodesulfurization process, Example 10 was repeated with 30 g of Ni/ZnO nanowire adsorbent, the diesel fuel feedstock was spiked to deliver 140 ppm thiophenic sulfur species (80 ppmw thiophene, 15 ppmw benzothiophene, 15 ppm dibenzothiophene, 15 ppmw 4-methyl dibenzothiophene, and 15 ppmw dibenzothiophene), the reactor temperature was set at 290° C. and the reactor pressurized to 30 bar. The spiked diesel fuel feedstock passed through the adsorbent initially at an LHSV=1 h$^{-1}$ and the H$_2$/oil=150 SCCM/ml. After about 35 hours on stream, the feed rate was adjusted to an LHSV=2 h$^{-1}$ for about 30 hours, with no significant change in adsorption observed. The LHSV was then adjusted to 0.5 h$^{-1}$ for about 5 hours, with no significant change in adsorption observed. After 75 hours on stream, the feed rate was returned to LHSV=1 h$^{-1}$ using the 140 ppm sulfur spiked diesel fuel for an additional 225 hours. As shown in FIG. 2, sulfur concentration at the outlet was decreased to less than 40 ppm. After 300 hours on stream, the feedstock was spiked to deliver 1500 ppm sulfur with the LHSV=1 h$^1$ and while maintaining all other reaction conditions. After an initial spike in sulfur output, the sulfur output level decreased, but sulfur breakthrough was still observed. After 440 hours on stream, the feed rate was adjusted to LHSV=0.5 h$^{-1}$ and the sulfur output was reduced to about less than 10 ppm.

The method of the present invention, and particularly using the Ni/ZnO nanowire adsorbent or the Ni$_{1-x}$Zn$_x$/ZnO nanowire adsorbent, has proven effective for long-term performance and sulfur pickup capacity. In field studies, it has been demonstrated that the nickel-zinc nanowire adsorbent sulfur removal efficiency was two-times greater than a nickel-zinc non-nanowire catalyst for reactions in the temperature range of 300-400° C. It has also been found that the lifetime of the nickel-zinc nanowire adsorbent is 1.5 times longer than a similar non-nanowire product. Based on the results from Example 10A, the sulfur pickup for the Ni/ZnO nanowire adsorbent of the present invention is found to be 223 mg sulfur/g catalyst after 570 hours of operation (a total of 6.7 g sulfur was picked up 30 g adsorbent), and the adsorbent was still active. As indicated in Table 6, this represents a significant improvement over the prior art.

TABLE 6

| Catalyst/Adsorbent | Reaction Conditions | Sulfur pickup capacity |
|---|---|---|
| Ni—ZnO[1] | FCC gasoline | 25.4 mg S/g catalyst |
| Ni—ZnO—Al$_2$O$_3$—SiO$_2$ prepared by coprecipitation[2] | Diesel fuel w 1187 ppm sulfur | 38.4 mg S/g catalyst |
| Ni—ZnO—ZSM-5 (1:1) prepared by incipient wetness impregnation[3] | Model gasoline fuel | 7.34 mg S/g catalyst |
| Ni/ZnO nanowire adsorbent[4] | Naphtha w 900-1000 ppm thiophene | 190 mg S/g catalyst |
| Ni/ZnO nanowire adsorbent[5] | Diesel fuel w 140-1500 ppm thiophene and refractory sulfur species | 223 mg S/g catalyst |

[1]Acta Pet. Sin. 2008, 24: 739-743
[2]Energy Fuels 2015, 29: 6057-6067
[3]Transactions of Tianjin University 2019, 25: 143-151
[4]Example 11 herein
[5]Example 10A herein Example 11

Figure 3:
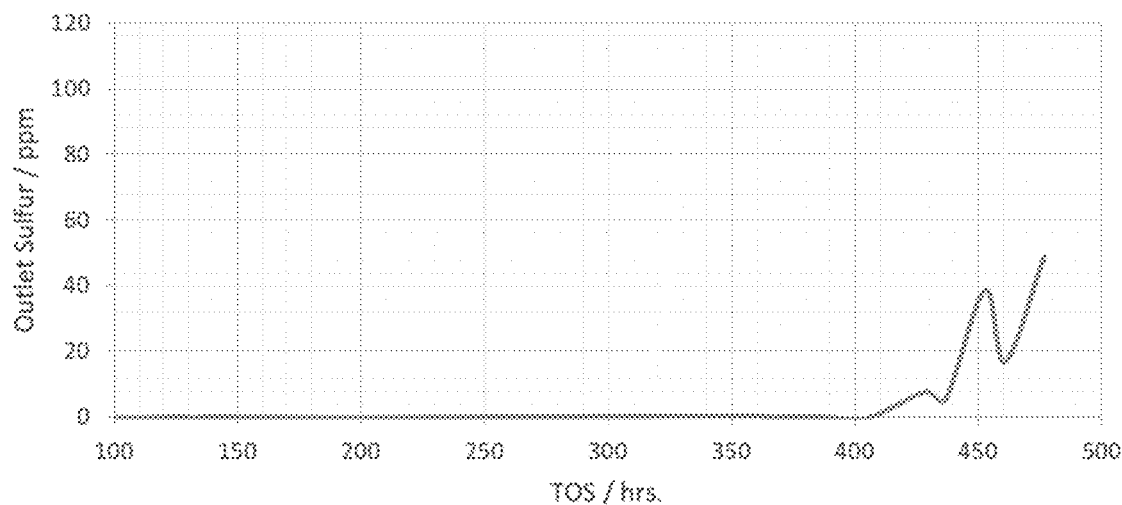
FIG. 3 is a graph showing the sulfur level detected at the reactor outlet using a Ni/ZnO adsorbent to desulfurize naphtha at P=20 bar, T=350° C., LHSV=1 h$^{-1}$, H$_2$=150 NL/L.
Figure 4:
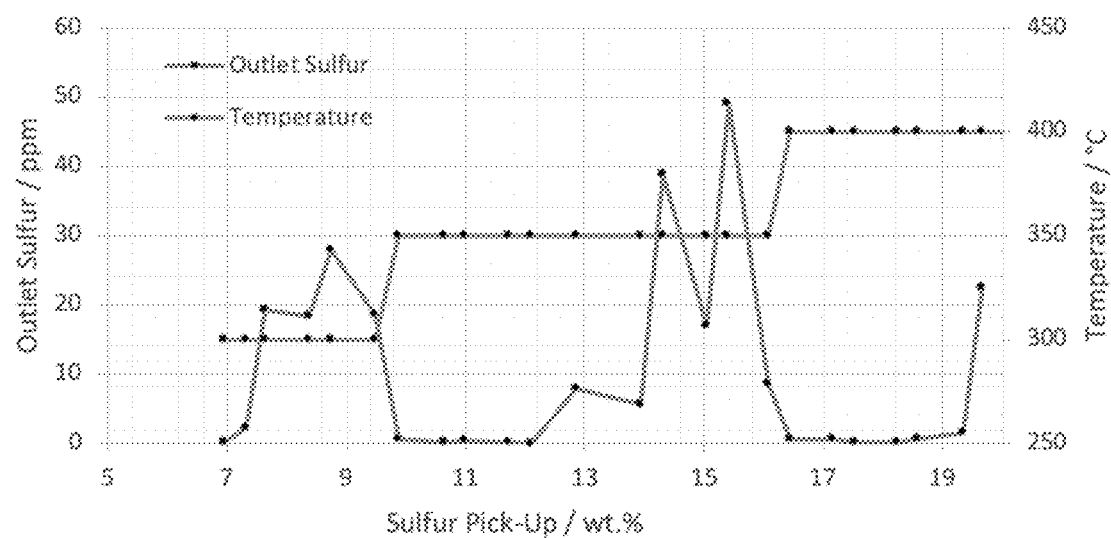
FIG. 4 is a graph showing the sulfur level uptake for the desulfurization of naphtha process using a Ni/ZnO adsorbent at P=20 bar, T=300° C., LHSV=1 h$^{-1}$, H$_2$=150 NL/L wherein the total sulfur uptake is higher than 19 wt. %.

Example 10 was repeated with 30 g of Ni/ZnO nanowire adsorbent, and with the diesel oil feedstock replaced with a naphtha feedstock having from 900 ppm to 1000 ppm thiophenic species. As shown in FIG. 3, the thiophenic species level decreases to 1 ppm for the first approximately 400 hours on stream. As shown in FIG. 4, the Ni/ZnO adsorbent continues to pick up sulfur until 19% by wt sulfur level. The theoretical sulfur pickup capacity for the product is 20% by wt, demonstrating the efficacy of the adsorbent.

Figure 5:
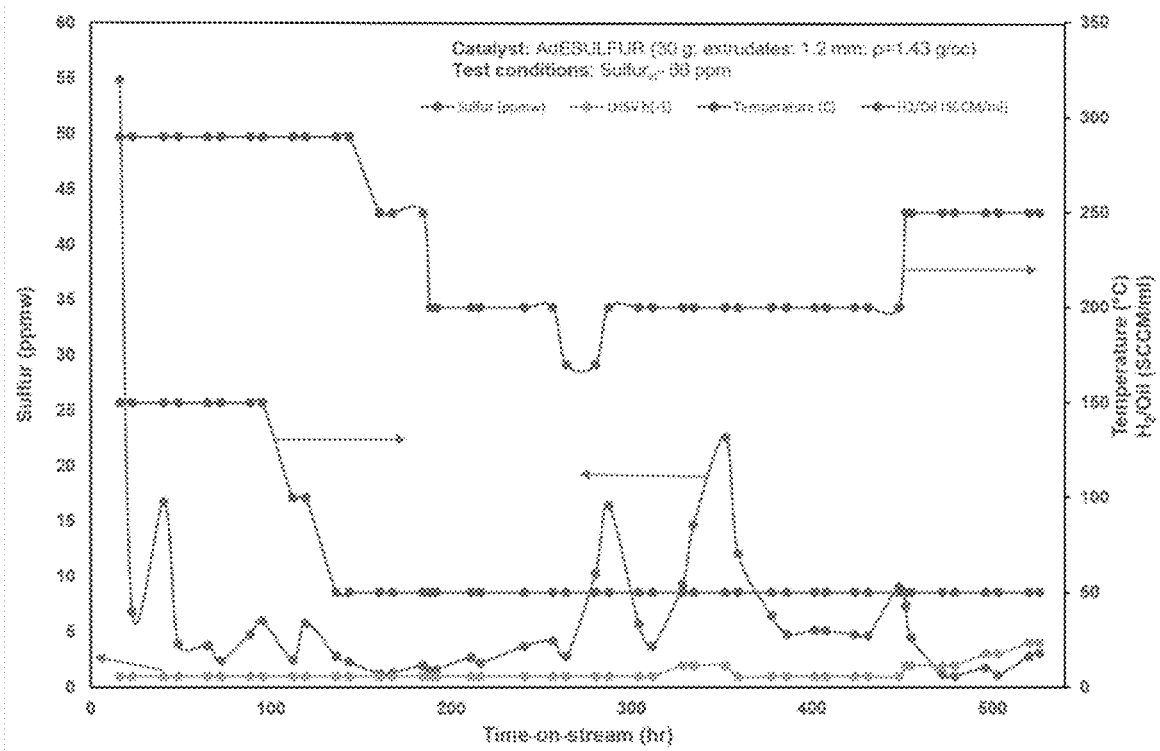
FIG. 5 is a graph showing the effect of temperature on a kerosene desulfurization process using a Ni/ZnO adsorbent.

The effect of H$_2$ to oil, or feedstock, ratio and of reaction temperature was evaluated using ASTM-1-K kerosene feedstock spiked with thiophene. As shown in FIG. 5, using the Ni/ZnO nanowire adsorbent sulfur removal is achieved under relatively mild reaction conditions. For example, sulfur is effectively removed from the feedstock at an H$_2$/oil=50 SCCM/ml (SCCM=standard cubic centimeters per minute; oil=feedstock) at temperatures as low as 200° C. Even after more than 450 hours on stream, the adsorbent can continue to pick up sulfur by maintaining the H$_2$/oil at 50 SCCM/ml and raising the temperatures to 250° C.

Example 12

Example 10 is repeated with 30 g of Ni/ZnO nanowire adsorbent, and with the diesel oil feedstock replaced with an ASTM-1-K kerosene feedstock spiked with thiophene to deliver a total sulfur level of 66 ppmw. The reactor temperature for the desulfurization process was set at 290° C. and the reactor pressurized to 30 bar. The spiked kerosene feedstock passed through the adsorbent at an LHSV=1 h$^{-1}$ and the H$_2$/oil=150 SCCM/ml. After 100 hours on stream, the H$_2$/oil was decreased to 100 SCCM/ml while maintaining the reactor temperature at 290° C. After an additional 24 hours on stream, the H$_2$/oil was decreased to 50 SCCM/ml while maintaining the reactor temperature at 290° C. After the system stabilized, approximately an additional 24 hours on stream, and while maintaining the H$_2$/oil at 50 SCCM/ml the reactor temperature was lowered over a period of about 48 hours to a temperature of 200° C. Sulfur output remained low and constant. After an additional 48 hours on stream and while maintaining the H$_2$/oil at 50 SCCM/ml, the reactor temperature dropped to a temperature of 170° C. Sulfur breakthrough was observed. Returning the reactor temperature to 200° C. while maintaining the H$_2$/oil at 50 SCCM/ml increased the sulfur adsorption. Increasing the reactor temperature to 250° C. while maintaining the H$_2$/oil at 50 SCCM/ml further increased the sulfur adsorption even after more than 450 hours on stream.

The Ni/ZnO nanowire adsorbent or the Ni$_{1-x}$Zn$_x$/ZnO nanowire adsorbent can be used to hydrogenate naphthalene to tetralin even in the presence of sulfur. Moreover, it has been found that the Ni/ZnO nanowire adsorbent and/or the Ni$_{1-x}$Zn$_x$/ZnO nanowire adsorbent can selectively do this hydrogenation, that is, the adsorbent selectively converts naphthalene to tetralin even at temperatures as low as 185° C. with a naphthalene conversion of about 92% and selectivity to tetralin about 83-93% over a time on stream of up to 170 hours.

Figure 6:
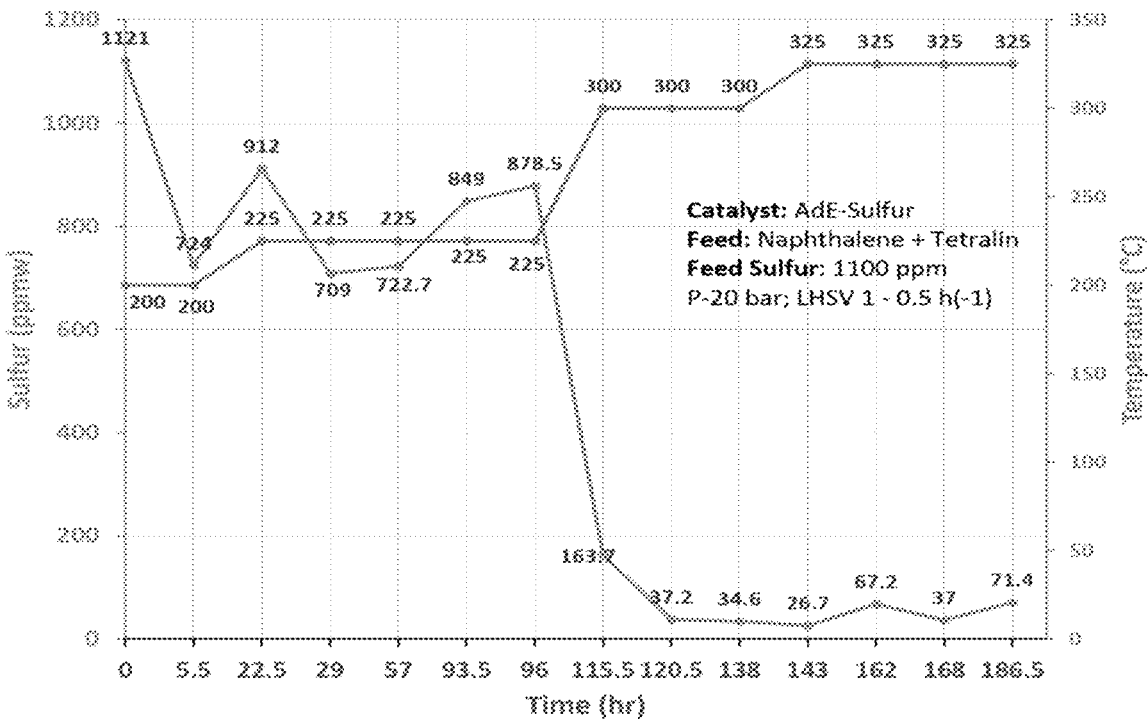
FIG. 6 is a graph showing the reaction temperature and the sulfur level detected at the reactor outlet using a Ni$_{1-x}$Zn$_x$/ZnO adsorbent to desulfurize naphthalene with P=20 bar, T=200-325° C., LHSV=0.5 h$^{-1}$; and, FIG. 7 is a graph showing naphthalene conversion and tetralin and decalin selectivities using a 12% Ni-88% ZnO adsorbent made according to the present invention.

Example 13A 30 g of the 12% Ni-88% ZnO adsorbent (cylindrical extrudates, D=3 mm, L=5 mm-8 mm; vol=6 cc) from Example 1 is packed into a fixed bed reactor. Prior to introduction of the feedstock, the adsorbent is pretreated in N$_2$ at 150° C. and then reduced at 430° C. in a hydrogen gas flow. The reactor is then cooled to a temperature of 200° C. and pressurized to 25 bar. The hydrocarbon feedstock, a 25% naphthalene and 75% tetralin blend spiked to deliver 1100 ppm sulfur, is pumped from a top inlet of the reactor and passes through the adsorbent at a LHSV of 0.5 to 1 h$^{-1}$ before exiting at a bottom outlet of the fixed bed reactor and being collected. After 5.5 hours on stream, the reactor temperature was raised to 225° C. with nominal effect on sulfur removal, as shown in FIG. 6. After an additional 90 hours on stream, the reactor temperature was raised to 300° C. which demonstrates significant sulfur removal. A further reactor temperature increase to 325° C. did not demonstrate further efficacy in sulfur removal. Exemplary results are shown in Table 7.

TABLE 7

| Temp (° C.) | Time on stream (hr) | Naphthalene Conv (%) | Product Selectivity (%) | |
|---|---|---|---|---|
| | | | Tetralin | Decalin |
| 185 | 28.5 | 92.7 | 98.3 | 1.7 |
| 185 | 41 | 88.7 | 99.1 | 0.9 |
| 185 | 51 | 86.7 | 98.6 | 1.4 |
| 200 | 66 | 91.5 | 97.4 | 2.6 |
| 200 | 73 | 94.0 | 89.7 | 9.9 |
| 200 | 90 | 91.1 | 97.8 | 2.7 |
| 200 | 96.5 | 92.3 | 86.5 | 13.5 |
| 200 | 138 | 92.7 | 89.1 | 10.9 |
| 200 | 145 | 95.6 | 92.0 | 7.6 |
| 200 | 162 | 93.1 | 94.4 | 5.6 |
| 200 | 167 | 92.7 | 82.6 | 17.0 |

Figure 7:
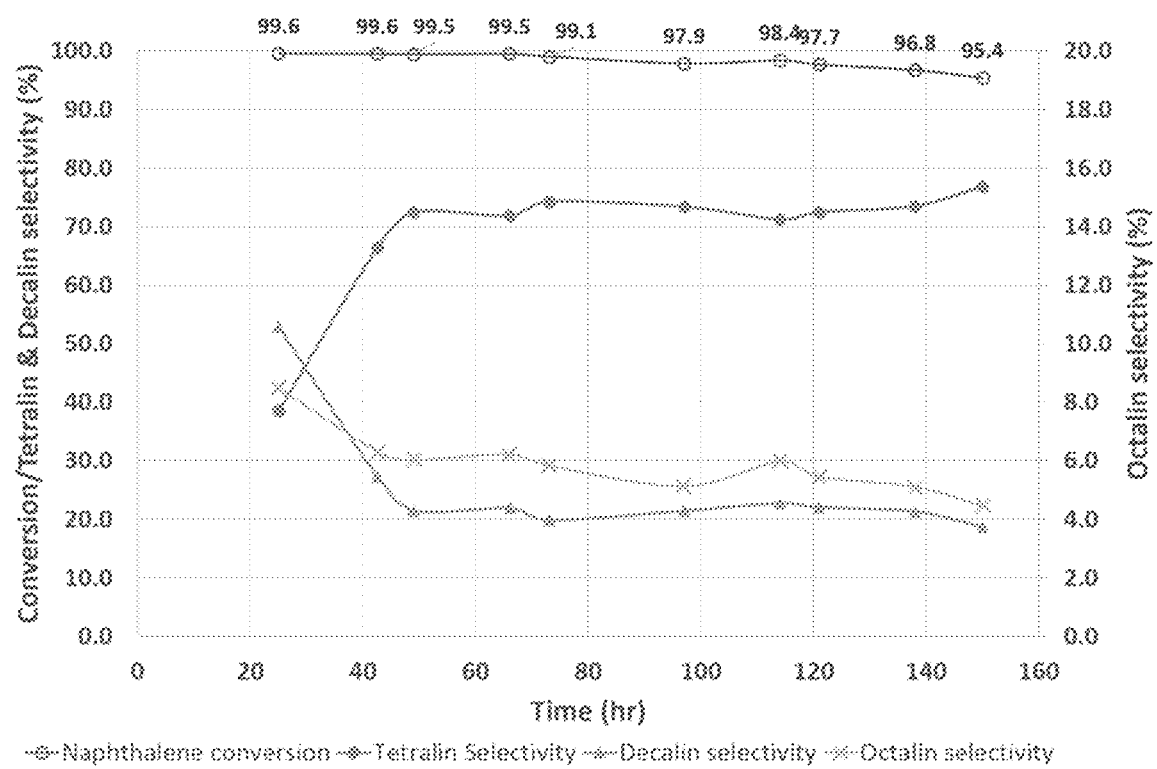

Example 13B 30 g of the 12% Ni-88% ZnO adsorbent (cylindrical extrudates, D=2 mm, L=5 mm-8 mm; vol=6 cc) from Example 1 is packed into a fixed bed reactor. Prior to introduction of the feedstock, the adsorbent is pretreated in N$_2$ at 150° C. and then reduced at 400° C. for 2 hours in a hydrogen gas flow. The reactor is then cooled to a temperature of 200° C. and pressurized to 25 bar. The hydrocarbon feedstock, a 18% naphthalene, 81.7% tetralin and 0.3% decaline blend with 15 ppm sulfur, is pumped from a top inlet of the reactor and passes through the adsorbent at a LHSV of 2 h$^{-1}$ before exiting at a bottom outlet of the fixed bed reactor and being collected. The naphthalene conversion and tetralin an decalin selectivities are shown in FIG. 7.

Natural gas contains 4-6 ppm sulfur in the form of H$_2$S, COS, methyl mercaptan, ethyl mercaptan and $^t$butyl mercaptan, and thiophene, as the major sulfur species. Deep desulfurization, reducing the sulfur level to less than 100 ppb, is necessary for most commercial applications. Traditionally, this is achieved by a two-step process: the first step is the HDS process using Ni—Mo catalyst or Co—Mo catalyst; the second step is removal of H$_2$S formed in the HDS process using a ZnO bed. To demonstrate that the nickel-decorated zinc oxide nanowire adsorbent is capable of deep desulfurization of a natural gas stream in a one-step process, a series of experiments were conducted using natural gas streams at varying reactor temperatures, reactor pressures, and at a gas hourly space velocity (GHSV) of 2000 h$^{-1}$ to 6000 h$^{-1}$, more preferably at a GHSV of 4000 h$^{-1}$ to 6000 h$^{-1}$, and most preferably at a GHSV of 5000 h$^{-1}$. As shown in the following examples, the adsorbent is effective for reducing the sulfur concentration in a natural gas stream in a single step process from about 3-20 ppmv to less than 50 ppbv, and preferably to less than 15 ppbv, and most preferably to less than 1 ppbv.

Example 14

Example 10 was repeated with 30 g of Ni/ZnO nanowire adsorbent (cylindrical extrudates, D=4.2 mm, L=5 mm-8 mm; vol=6 cc), and reduced at 400° C. for 4 hours, and with the diesel oil feedstock replaced with a natural gas feedstock having from up to 30 ppm sulfur. The reactor is then heated to a temperature of 310° C. at atmospheric pressure. The natural gas based mixed gas feedstock then passes through the nanowire oxide adsorbent at atmospheric pressure and at a gas feed flow rate of CH$_4$=149 cc/min and H$_2$=24 cc/min. The mixed feedstock composition is: CH$_4$: 50%-90%; H$_2$: 10%-15%; CO$_2$: 0-5%; water vapor: 0-10%; N$_2$: 0-10%, with a mixture of sulfur species. Table 8 shows the sulfur concentration from samples recovered at the outlet after various times on-stream.

TABLE 8

| Time on stream (h) | Sulfur analysis at outlet (ppm) | | | | | |
|---|---|---|---|---|---|---|
| | H$_2$S | MM | DMS | CS$_2$ | TBM | TP |
| Feed gas | 2.58 | 0.258 | 0.26 | 0.43 | 2.15 | 0.13 |
| 3 | 0 | 0 | 0 | 0 | 0 | 0 |
| 21 | 0 | 0 | 0 | 0 | 0 | 0 |
| 29 | 0 | 0 | 0 | 0 | 0 | 0 |
| 44.5 | 0 | 0 | 0 | 0 | 0 | 0 |

H$_2$S = hydrogen sulfide;
MM = methyl mercaptan;
DMS-dimethyl sulfide;
CS$_2$ = carbon disulfide;
TBM = tertiary butyl mercaptan;
TP = thiophene

Example 15

Example 14 was repeated with 30 g of Ni/ZnO nanowire adsorbent (cylindrical extrudates, D=1.2 mm, L=5 mm-8 mm; vol-6 cc) except the reactor is heated to a temperature of 350° C. at atmospheric pressure and the natural gas based mixed gas feedstock then passes through adsorbent at a GHSV of 2000 h$^{-1}$. Table 9 shows the sulfur concentration from samples recovered at the outlet after various times on-stream.

TABLE 9

Sulfur analysis at outlet

| Time on stream (h) | $H_2S$ | MM | DMS | $CS_2$ | TBM | TP |
|---|---|---|---|---|---|---|
| Feed gas | 112 ppb | — | 698 ppb | 258 ppb | 1.31 ppm | 0.1 ppm |
| 8 | 0 | 0 | 0 | 0 | 0 | 0 |

$H_2S$ = hydrogen sulfide;
MM = methyl mercaptan;
DMS-dimethyl sulfide;
$CS_2$ = carbon disulfide;
TBM = tertiary butyl mercaptan;
TP = thiophene

Example 16

Example 10 was repeated with 30 g of Ni/ZnO nanowire adsorbent (cylindrical extrudates, D=1.2 mm, L=5 mm-8 mm; vol=6 cc), the diesel fuel feedstock was replaced with 98 vol % natural gas+2 vol % hydrogen and the gas was fed into the reactor at a GHSV=2000 h$^{-1}$, the reactor temperature was set at 350° C. and the reactor pressurized to 34+/−2 bar. Table 10 shows the sulfur concentration from samples recovered at the outlet after various times on-stream.

TABLE 10

Sulfur analysis at outlet (ppm)

| Time on stream (h) | $H_2S$ | MM | DMS | $CS_2$ | TBM | TP |
|---|---|---|---|---|---|---|
| Feed gas | 3.0 | 0.3 | 0.3 | 0.5 | 2.5 | 0.15 |
| 4 | 0.05 | 0 | 0 | 0 | 0 | 0.07 |
| 23 | 0.13 | 0 | 0 | 0 | 0 | 0 |
| 70 | 0.14 | 0 | 0 | 0 | 0 | 0 |

Feed gas also contains 0.15 ppm carbonyl sulfide (COS)
$H_2S$ = hydrogen sulfide;
MM = methyl mercaptan;
DMS-dimethyl sulfide;
$CS_2$ = carbon disulfide;
TBM = tertiary butyl mercaptan;
TP = thiophene

Example 17

Example 14 was repeated with 30 g of Ni/ZnO nanowire adsorbent (cylindrical extrudates, D=4.2 mm, L=5 mm-8 mm; vol=6 cc), except the feedstock is natural gas with 10 ppm tetrahydrothiophene in the presence of 3% $CO_2$. The natural gas gas feedstock passes through the adsorbent at atmospheric pressure and at a gas feed flow rate of $CH_4$=148.5 cc/min, $CO_2$=6.0 cc/min, $N_2$=7.8 cc/min and $H_2$=25.8 cc/min. In one run, 5.5 vol % water vapor is added to the feedstock at a gas flow rate of 10 cc/min. Table 10 shows the sulfur concentration from samples recovered at the outlet. Although not included in Table 10, the 290° C. test extended to more than 550 hours on stream with no sulfur detected and the 310° C. test extended to more than 412 hours on stream with no sulfur detected at the outlet.

As also indicated in Table 11, the nickel-decorated zinc oxide nanowire adsorbent not only removes sulfur from the natural gas stream, but it is also effective for conversion of carbon dioxide in the natural gas to methane.

TABLE 11

| | | Sulfur analysis at outlet (ppm) | | | |
|---|---|---|---|---|---|
| | | With Water Vapor | | Without Water Vapor | |
| Temp (° C.) | Time on stream (h) | $CO_2$ Conv (%) | Sulfur (ppmv) | $CO_2$ Conv (%) | Sulfur (ppmv) |
| 270 | 4 | | | 36 | 0 |
| 270 | 8 | | | 34.4 | 0 |
| 270 | 24 | 6.3 | 0 | not tested | |
| 290 | 24 | 9.2 | 0 | | |
| 290 | 486 | 4.5 | 0 | not tested | |
| 290 | 507 | 4.3 | 0 | not tested | |
| 290 | 526 | 4.3 | 0 | not tested | |
| 310 | 4 | | | 44.8 | 0 |
| 310 | 8 | | | 44.3 | 0 |
| 310 | 18 | 15.8 | 0 | not tested | |
| 310 | 296 | 14.4 | 0 | not tested | |
| 310 | 388 | 14.2 | 0 | not tested | |

The reactions described herein may be carried out in the packed-bed reactor process or batch reactor process at moderate pressure and temperatures.

As demonstrated herein, the $Ni_{1-x}Zn_x$/ZnO nanowire catalyst is active in desulfurization of natural gas with a sulfur level of 6-7 ppm, the sulfur derived from a variety of sources, including but not limited to $H_2S$, COS, $CS_2$, mercaptans, and thiophene, at atmospheric pressure and as well as at 35 bar, conditions that are relevant to fuel cells and $H_2$/syngas production plants respectively. As demonstrated herein, the $Ni_{1-x}Zn_x$/ZnO nanowire catalyst is active in desulfurization of natural gas under more rigorous conditions, including relatively low reaction temperatures, e.g. 150° C.-200° C., and gas hourly space velocities from 2000 h$^{-1}$ to 6000 h$^{-1}$ for long on-stream times. As is known in the art, the spent catalysts may be harvested for metal recovery.

The metal oxide nanowires with the catalytically-active metal particles of the present invention are intended to be used in a desulfurization process without adding external hydrogen. The use of nanowire-structured adsorbents is expected to result in improved mass-transfer and an improved mechanical behavior during high temperature operation. Further, these nanowires are expected to offer rapid reaction rates that overcome the diffusion limitations of conventional pellet-based adsorbents and allow all of the material to be used efficiently. It is anticipated that the adsorbents of the present invention may be used in the desulfurization of hydrocarbon fuels commonly found in the oil refining including, but not limited to, waste lube oil, light cycle oil, diesel, jet fuel, kerosene, and combinations thereof.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

The terms "a", "an", and "the" refer to "one or more" when used in the subject specification, including the claims. The term "ambient temperature" as used herein refers to an environmental temperature of from about 0° F. to about 120'F, inclusive.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

All compositional percentages used herein are presented on a "by weight" basis, unless designated otherwise. Specific compositions relevant to the titanium(IV) oxide nanowires with catalytically-active metal sulfide particles composition are provided herein for the purpose of demonstrating the invention, but these compositions are not intended to limit the scope of the invention. It is understood that one skilled in the art may make alterations to the embodiments shown and described herein without departing from the scope of the invention.

What is claimed is:

1. A method for the treatment of a liquid sulfur-containing hydrocarbon feedstock, the method comprising:
   a. providing an adsorbent comprising a zinc oxide nanowire decorated with a decorating metal selected from nickel, nickel-zinc alloy, cobalt, molybdenum, platinum, copper, nickel-copper alloy, and combinations thereof;
   b. packing a reactor bed with the adsorbent;
   c. pretreating the decorating metal of the adsorbent by heating the adsorbent in a reactor while flowing nitrogen gas ($N_2$) over the adsorbent for a predetermined time;
   d. after pretreating the decorating metal, reducing the decorated metal of the adsorbent by starting a flow of hydrogen gas ($H_2$) over the adsorbent as the reactor temperature is raised to a predetermined temperature and then holding the adsorbent at the predetermined temperature with a $H_2$ gas flow for a predetermined time period;
   e. after reducing the decorating metal, cooling the reactor to a desulfurization temperature between 220° C. and 425° C. and stopping the hydrogen gas flow when the desired desulfurization temperature is reached;
   f. passing the liquid sulfur-containing hydrocarbon feedstock through the adsorbent without adding external hydrogen and allowing the adsorbent to remove sulfur-containing compounds from the sulfur-containing hydrocarbon feedstock; and,
   g. collecting the treated liquid hydrocarbon feedstock.

2. The method of claim 1 wherein the sulfur-containing compounds are selected from thiophene, benzothiophene, dibenzothiophene, methyl dibenzothiophene, dimethyldibenzothiophene, $H_2S$, COS, methyl mercaptan, ethyl mercaptan and $^t$butyl mercaptan, and combinations thereof.

3. The method of claim 1 wherein the adsorbent has a decorating metal loading of from 3 wt % to 20 wt %.

4. The method of claim 1 wherein the metal oxide nanowire concentration is from about 55 wt % to about 88 wt %.

5. The method of claim 1 wherein at step (c) the reactor is heated to 150° C. for 2 hours with the nitrogen flow.

6. The method of claim 1 wherein at step (d) the reactor is heated to between 400° C. and 430° C.

7. The method of claim 1 wherein the adsorbent further comprises a binder selected from the group consisting of alumina, bentonite clay and combinations thereof, and wherein the binder comprises up to 30 wt % of the adsorbent composition.

8. The method of claim 1 wherein the adsorbent absorbs at least 150 milligrams sulfur species per gram adsorbent.

9. The method of claim 1 wherein the sulfur-containing hydrocarbon feedstock is selected from waste lube oil, transmix fuels, diesel fuel, gasoline, natural gas, light cycle oil, jet fuel, naphtha, kerosene, and combinations thereof, and at step (f) the feedstock passes through the adsorbent at a pressure of from atmospheric pressure to 30 bar, and at a liquid hourly space velocity of 0.5 $h^{-1}$ to 4 $h^{-1}$.

10. The method of claim 2 wherein the hydrocarbon feedstock comprises thiophenic sulfur species selected from thiophene, benzothiophene, dibenzothiophene, methyl dibenzothiophene, dimethyldibenzothiophene, and combinations thereof, and the thiophenic sulfur species have a concentration of from 500 ppm to 1500 ppm.

11. The method of claim 1 wherein the sulfur-containing hydrocarbon feedstock is natural gas and at step (f) the feedstock passes through the adsorbent at a temperature of 310° C. -350° C. and at a pressure of from atmospheric pressure to 34+/−2 bar.

12. The method of claim 11 wherein the adsorbent removes sulfur-containing compounds from the hydrocarbon feedstock, and wherein the sulfur-containing compounds are selected from thiophene, $H_2S$, COS, methyl mercaptan, ethyl mercaptan and $^t$butyl mercaptan, and combinations thereof from the feedstock to deliver a sulfur level of less than 100 ppb.

13. The method of claim 1 wherein the sulfur-containing hydrocarbon feedstock is a sulfur-containing naphthalene feedstream, and at step (f) the feedstock passes through the adsorbent at a liquid hourly space velocity of 0.5 $h^{-1}$ to 2 $h^{-1}$.

* * * * *